United States Patent [19]
Holzermer

[11] Patent Number: 5,373,546
[45] Date of Patent: Dec. 13, 1994

[54] FILTER CHANGER

[75] Inventor: Guenter Holzermer, Erlangen, Germany

[73] Assignee: Siemens Aktiengesellschaft, Munich, Germany

[21] Appl. No.: 113,249

[22] Filed: Aug. 30, 1993

[51] Int. Cl.⁵ ............................................. G21K 3/00
[52] U.S. Cl. ..................................... 378/157; 378/156
[58] Field of Search .................................. 378/156–159

[56] References Cited

U.S. PATENT DOCUMENTS

| | | |
|---|---|---|
| 3,248,547 | 4/1966 | Van De Geijn .................... 378/159 |
| 4,627,089 | 12/1986 | Menor et al. ........................ 378/159 |
| 4,672,652 | 6/1987 | Huttenrauch et al. . | |
| 4,914,685 | 4/1990 | Yanome . | |

FOREIGN PATENT DOCUMENTS 2024796 10/1973 Germany .
3500812 7/1986 Germany .
1258028 12/1971 United Kingdom .

Primary Examiner—Craig E. Church
Attorney, Agent, or Firm—Hill, Steadman & Simpson

[57] ABSTRACT

A filter changer for a radiation transmitter comprises a filter which is adjusted between a first position out of the beam path of the radiation transmitter to a second position in the beam path. The changer includes guides for guiding the filter for movement along a linear path, an arm having one end engaging the filter and the other end engaging an actuating arrangement so that when the arm is rotated against a spring, the filter is moved from the first to the second position and when the arm is released from the actuating arrangement, the spring biases the arm and filter back into the first position.

5 Claims, 2 Drawing Sheets

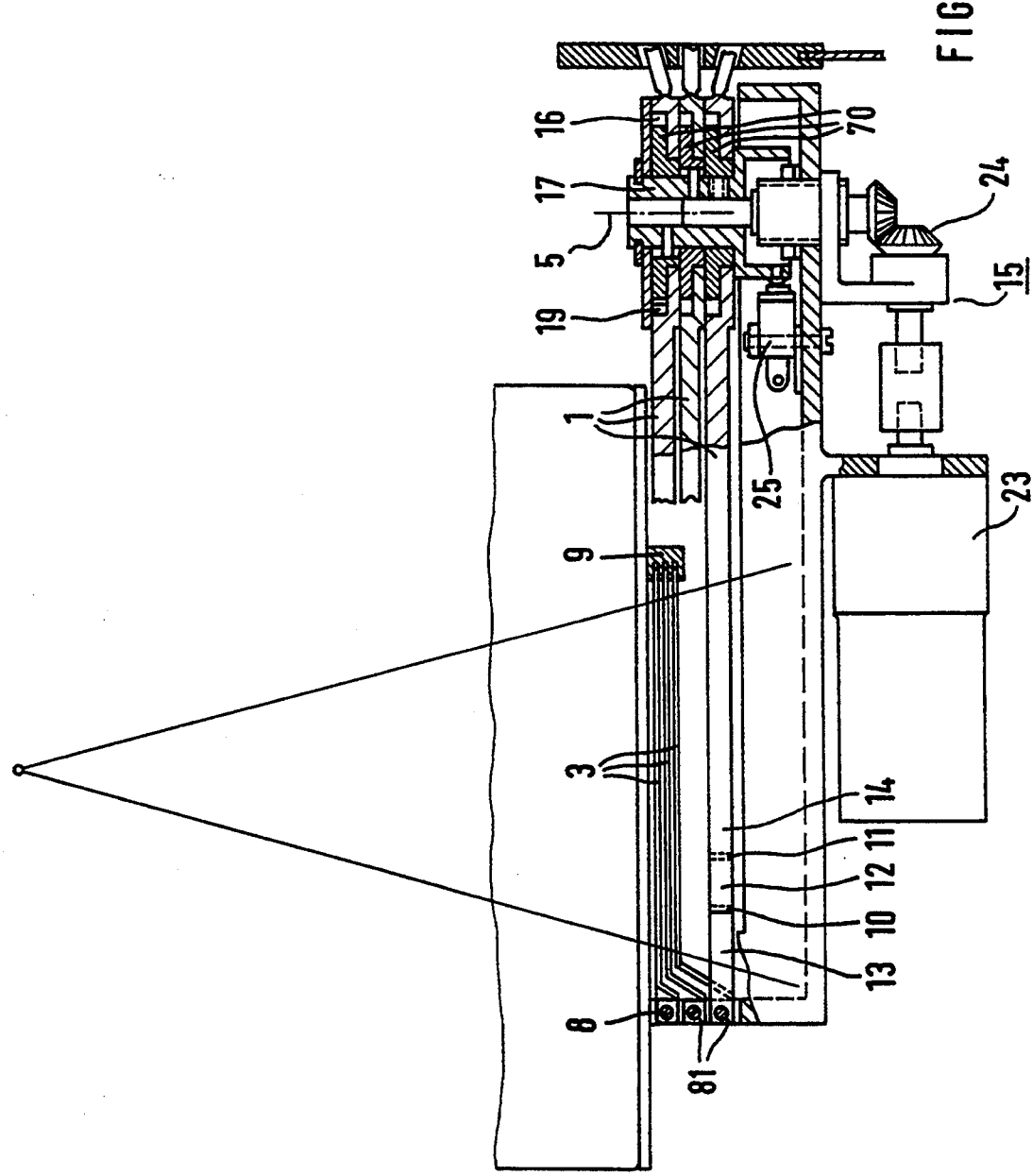

FILTER CHANGER

BACKGROUND OF THE INVENTION

The present invention is directed to a filter changer for a radiation transmitter having a filter which is adjustable into the beam path of the radiation transmitter via an articulation.

U.S. Pat. No. 4,672,652, whose disclosure is incorporated herein by reference thereto and which claims priority from German Patent Application 35 00 812, discloses an x-ray means having a semi-transparent diaphragm that comprises individual lamellae that lie parallel against one another and lie on both sides of a slot. These lamellae are individually adjustable in a planar direction dependent on the size of the article to be observed. The adjustment of the lamellae can occur by respective motors. An individual adjustment of the lamellae can also be obtained in that a motor is provided for a number of diaphragms and this motor drives a drum in which is at least one coupling magnet is provided that will couple the lamellae to the drum. The lamellae preferably comprise a region that is constructed as a rack gear and are in connection with the drum which is a toothed drum.

SUMMARY OF THE INVENTION

An object of the present invention is to provide a filter changer that can be cost-beneficially manufactured and provides a compact structure.

This object is achieved by a filter changer for a radiation transmitter, which filter changer comprises a pair of guide ways slidably receiving a filter for movement on a linear path between a first position out of a beam path to a second position in the beam path, biasing means for urging the filter into the first position, and articulation means for moving the filter between the first and second positions including an arm having a first end acting on the filter and a second end engaging a shaft around which the arm is pivoted so that pivoting of the arm against the force of the biasing means will move the filter into the second position.

Since no drums or tooth racks need to be manufactured, the present invention has a cost-beneficial manufacture due to the mechanically uncomplicated structure of the filter changer. Because the arm can extend as an extremely flat structure which is different than the drum structure, this structure requires a low volume.

It is advantageous when the arm acting on the filter is connected to the filter by a first hinge, an intermediate part and a second hinge so that a guidance of the arm transversely relative to the adjustment direction of the filter can be foregone, which is required when the arm is pivoted around the shaft. The motion relative to the filter produced due to the pivot of the arm is compensated by the pivoting and movement of the intermediate part.

The filter changer can be especially advantageously operated when the adjustment means acts on the second end of the arm by a dog pivoting the arm when the dog engages a dog or nose on the arm to form a releasable connection, which will release the arm when the shaft exceeds a predetermined adjustment distance.

Additional improvements in the operation of the filter changer occur when the adjustment means is implemented as an electromechanical adjustment means, when the filter is adjusted from the first into the second position due to the drive of the electromechanical adjustment means, when the drive of the adjustment means is interrupted in the second position, and when the arm is released due to a renewed drive of the adjustment means beyond or past the second position.

It is advantageous in order to be able to effect different filterings when additional filters are adjusted into the beam path and are provided in the filter changer. These additional filters are adjusted into the second position by an allocated arm which is pivoted around the shaft, and when the adjustment means comprises a dog allocated to each of the arms, the filters are successively adjusted into the second position by driving the electromechanical adjustment means.

Other advantages and features of the invention will be readily apparent from the following description of the preferred embodiments, the drawings and claims.

BRIEF DESCRIPTION OF THE DRAWINGS

FIG. 2 is a partial side view with portions broken away for purposes of illustration of the filter changer of FIG. 1.

DESCRIPTION OF THE PREFERRED EMBODIMENTS

Figure 1:
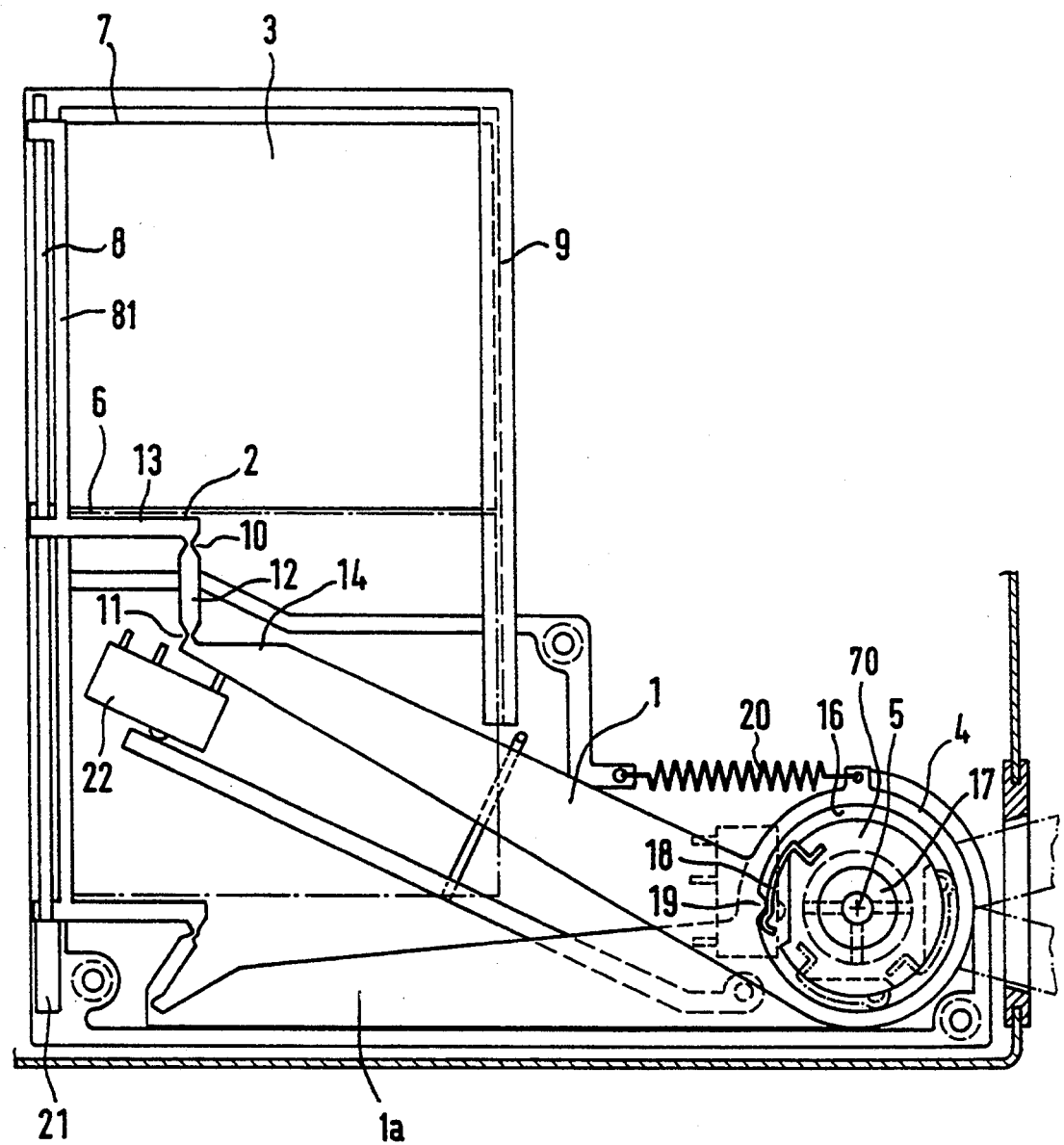
FIG. 1 is a partial plan view with portions broken away for purposes of illustration of a filter changer in accordance with the present invention.

The principles of the present invention are particularly useful when incorporated in a filter changer illustrated in FIGS. 1 and 2. The filter changer of the invention has an articulation or linkage which includes an arm 1 having a first end 2 which is acting on a filter 3 and has a second end 4 which will act with a shaft 5 around which the arm can be pivoted or rotated. Due to the rotation of the arm from a first position shown by an arm 1a, the filter can be adjusted from a first position 6, which is shown in broken lines and in which the filter is located outside of the beam path of a radiation transmitter. When rotated from this position in a clockwise direction to the position of the arm 1 of FIG. 1, the filter 3 is then located in a second position 7 shown in solid lines wherein the filter is located in the beam path. To guide the filter as it moves between the first and second positions, guides 8 and 9 are provided on opposite sides of the filter with the guide 9 being basically a channel receiving an edge of the filter and the guide 8 being a pin-type arrangement which slidably receives a member 81 connected to one side of the filter 3. Guides 8 and 9 provide a guidance for either a quadratic or rectangular-shaped filter 3. The first end 2 of the arm 1 is illustrated as being connected by a first region 13 to the member 81. This first region 13 is connected to a second region 14 of the arm 1 by a first hinge 10, an intermediate part 12 and a second hinge 11. Since a relative motion between the first region 13 and the second region 14 of the first end 2 caused by pivoting of the arm 1 is compensated by the pivoting of the intermediate part 12 around the axes of the hinges 10 and 11, the first end 2 of the arm 1 can, thus, be held in firm connection to the filter 3.

The pivot of the arm 1 occurs with an adjustment means 15 which is shown in greatest detail in FIG. 2. As shown in FIG. 1, the adjustment means 15 includes a drum 17 which is rotated with the shaft 5 around an axis of a shaft 5 and is received in a circular disk-shaped recess 16 of the second end 4 of the arm 1. This drum 17 bears a tongue-shaped element 18 that forms a resilient dog. When the roller or drum is rotated by the shaft 5 in a clockwise direction, the tongue-shaped spring element 18 will engage a nose 19 provided on the circular disk-shaped recess 16 to form a connection and to pivot the arm against the force of the spring 20 which acts on the arm 1. With further rotation of the drum 17 by the shaft 5, the filter 3 will be adjusted from the first position 6 into the second position 7 against the force of the biasing means formed by the spring 20. When the filter 3 is located in the second position, then a tongue-shaped spring element 18 will pass under the nose 19 if there is continued rotation of the drum 17 so that the arm will be adjusted in the counter-clockwise rotation by the biasing force of the spring element 20. It is, therefore, advantageous that a dampening means 21, with which the acceleration of the arm 1 is decelerated being provided in the end region of the first position and, as illustrated, is located adjacent the pin or rod 8.

When the filter 3 is to be held in the second position 7, then a latch is to be provided to provide a mechanical adjustment means and a switch means 22 that suppresses the drive of the electromechanical means 15 when in the second position, is provided. The adjustment of the filter 3 into the first position is obtained by the adjustment of the mechanical adjustment means out of the latch or by a renewed rotation of the electromechanical means 15.

Within the framework of the invention, the filter changer, as shown in FIG. 2, can comprise additional filters with correspondingly additional arms that are adjusted into the first and second positions via the electromechanical adjustment means 15. To this end, the electromechanical adjustment means has a motor 23 which can be a stepping motor and which will rotate the drum 17 via a gear arrangement 24. As illustrated in FIG. 1, a plurality of spring element 18 forming the dogs for engaging respective noses are arranged around the circumference of the drum and are offset, for example, in an annular direction by 90°. However, it should be noted that these dogs are located on different disks 70, which are axially spaced along the axis of the shaft or drum 17. The filters can, thus, be successively adjusted into the beam path of the radiation transmitter by the electromechanical adjustment means 15 that needs only one rotational direction. The return of the additional filters into the first position 6, likewise, occurs with the spring element acting on the respective arm for that filter. Every additional arm has switch means allocated to it that will stop the drive of the electromechanical means 15 when the allocated filter is located in the second position. A filter changer can, thus, be manufactured that, for example, comprises three different filters for filtering the radiation.

When no filtration should occur, then, after the third filter has been located in the second position, the motor 23 is again rotated so that the third filter will be returned to the first position by the spring element of the biasing means. The shaft of the motor 23 and, thus, the drum 17 are then adjusted to a defined position in which an interruption of the drive of the motor 23 is obtained by a light barrier or switch 25.

The arm and, in particular, the first and second hinges 10 and 11, as well as the intermediate piece or part 12 are especially advantageously manufactured as a one-piece plastic part. The hinges are thereby manufactured as film hinges and, thus, the plastic part comprises a greatly reduced cross section in the region of the hinges. It should also be noted that the member 81 is also integral with the first region 13 of the arm 1.

Although various minor modifications may be suggested by those versed in the art, it should be understood that I wish to embody within the scope of the patent granted hereon all such modifications as reasonably and properly come within the scope of my contribution to the art.

I claim:

1. A filter changer for a radiation transmitter, said changer comprising a filter, adjustable guide ways arranged on opposite sides of the filter engaging the filter to provide an adjustment path between a first position removed from the beam path of the radiation transmitter to a second position in the beam path, articulation means for shifting the filter between said first and second positions including an arm having one end acting on the filter and another end engaging a shaft around which the arm pivots, biasing means for biasing the arm and the filter to the first position, and said articulation means including means to pivot the arm against the biasing means to move the filter to the second position.

2. A filter changer according to claim 1, wherein the arm adjacent the first end has a portion attached to the filter, said portion being connected to an intermediate part by a first hinge and the intermediate part is connected to the remainder of the arm by a second hinge.

3. A filter changer according to claim 2, wherein the means for pivoting the arm against the biasing means includes a releasable connection including a dog engaging a nose, said connection being released when the shaft and dog are moved beyond a predetermined position which determines the position of the arm to place the filter in the second position.

4. A filter changer according to claim 3, which includes an additional filter being adjustable between a first and second position, said additional filter being provided with an additional arm pivotable around the shaft, said arm being connected to the adjustment means by a disconnectible coupling including a dog allocated to that arm and spaced so that the additional filter is moved to the second position after the first-mentioned filter has returned to the first position.

5. A filter changer according to claim 1, wherein the means for moving the arm includes an electromechanical adjustment means, said filter being adjusted between the first and second positions due to the drive of the electromechanical adjustment means, said electromechanical adjustment means being interrupted in its drive when the filter assumes the second position and the arm being released from a connection to the electromechanical adjustment means when the means is rotated past the predetermined position for the second position of the filter.

* * * * *